United States Patent
Salminen et al.

(10) Patent No.: US 8,658,156 B2
(45) Date of Patent: Feb. 25, 2014

(54) SUPPLEMENTION OF MATERNAL DIET

(75) Inventors: Seppo Salminen, Turku (FI); Erika Isolauri, Nrumijarvi (FI); Kirsi Laitinen, Kaarina (FI)

(73) Assignee: Nestec S.A., Vevey (CH)

( * ) Notice: Subject to any disclaimer, the term of this patent is extended or adjusted under 35 U.S.C. 154(b) by 662 days.

(21) Appl. No.: 12/667,653

(22) PCT Filed: Jul. 4, 2008

(86) PCT No.: PCT/EP2008/058640
§ 371 (c)(1),
(2), (4) Date: Jan. 4, 2010

(87) PCT Pub. No.: WO2009/004076
PCT Pub. Date: Jan. 8, 2009

(65) Prior Publication Data
US 2010/0178281 A1    Jul. 15, 2010

(30) Foreign Application Priority Data
Jul. 5, 2007    (EP) ..................................... 07111871

(51) Int. Cl.
*A01N 63/00* (2006.01)
(52) U.S. Cl.
USPC ..................................... 424/93.45; 435/252.9
(58) Field of Classification Search
None
See application file for complete search history.

(56) References Cited

U.S. PATENT DOCUMENTS

| 2006/0088574 A1 | 4/2006 | Manning et al. |
| 2006/0128714 A1 | 6/2006 | Wu et al. |
| 2006/0233772 A1 | 10/2006 | Herz et al. |

FOREIGN PATENT DOCUMENTS

| CN | 1357360 | 7/2002 |
| CN | 1380902 | 11/2002 |
| EP | 1424075 A2 | 6/2004 |
| WO | 01/88095 | 11/2001 |
| WO | WO0238165 A1 | 5/2002 |
| WO | WO03082306 A1 | 10/2003 |
| WO | WO2004112508 A1 | 12/2004 |
| WO | WO2006091103 A2 | 8/2006 |
| WO | WO2006108824 A1 | 10/2006 |
| WO | WO2007043933 A1 | 4/2007 |

OTHER PUBLICATIONS

Kalliomäki et al., Lancet, 2001, vol. 37, p. 1076-1079.*
Lee et al., Journal of Applied Microbiology, published online Apr. 2007, vol. 103, p. 140-1146.*
Huet et al., "Evaluation of a formula with low protein content and supplemented with probiotic agents after breast milk weaning," Archives de pediatrie 13 (2006), pp. 1309-1315.
Lee et al., "Human originated bacteria, *Lactobacillus rhamnosus* PL160, produce conjugated linoleic acid and show anti-obesity effects in diet-induced obese mice," Biochimica et Biophysica Acta, vol. 1761 (2006), pp. 736-744.
International Search Report PCT/EP2008/058640 mailing date Aug. 11, 2009, 7 pages.
Written Opinion of the International Search Authority PCT/EP2008/0588640 mailing date Aug. 11, 2009, 10 pages.

* cited by examiner

*Primary Examiner* — Kade Ariani
(74) *Attorney, Agent, or Firm* — K&L Gates LLP

(57) ABSTRACT

The use of probiotic bacteria in the manufacture of a composition for administration to a woman in at least the third trimester of pregnancy for prevention of gestational diabetes, normalizing plasma glucose concentration and/or increasing insulin sensitivity.

8 Claims, 1 Drawing Sheet

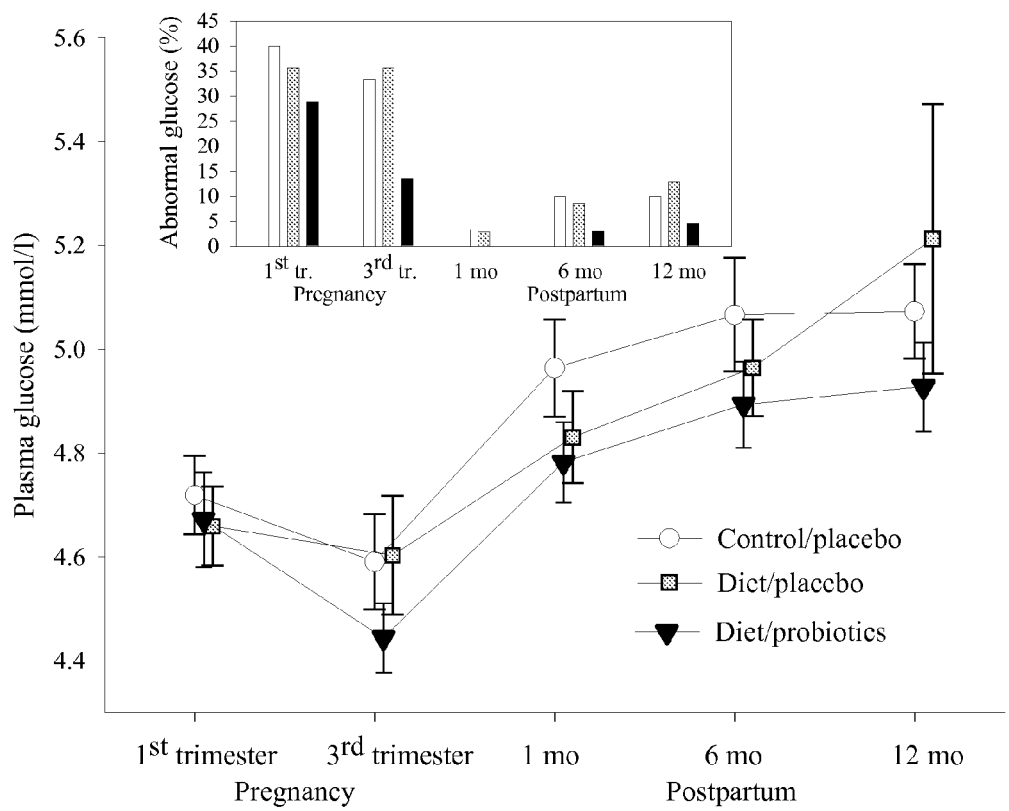

SUPPLEMENTION OF MATERNAL DIET

FIELD OF THE INVENTION

This invention relates to the use of probiotic bacteria in the manufacture of a nutritional supplement or special dietary food for pregnant women to normalise plasma glucose concentrations, increase insulin sensitivity and reduce the risk of development of gestational diabetes.

BACKGROUND TO THE INVENTION

Pregnancy is associated with metabolic adjustments including weight gain and changes in glucose and lipid metabolism. This regulatory fine-tuning takes place to support foetal growth and consequently a successful outcome of pregnancy but they may have long-term effects on maternal and child health such as disturbances in glucose metabolism.

Early pregnancy is characterized by normal tolerance to glucose and insulin. In late pregnancy, by contrast, an increase in serum insulin concentration accompanied by the development of insulin resistance is observed. These metabolic adaptations support foetal growth by shunting metabolic fuels to the foetus instead of the mother. However, in some pregnant women this adaptation process is exaggerated leading to impaired glucose tolerance. These individuals have an increased risk of developing gestational diabetes mellitus and consequently adult Type 2 diabetes mellitus. Impaired glucose metabolism in a pregnant woman may be associated with macrosomia and risk of impaired glucose tolerance in her child. These conditions may develop even when maternal glucose tolerance is within normal reference ranges i.e. not classified as gestational diabetes mellitus. This pathophysiology—higher than optimal glucose levels—is more common than might be anticipated and constitutes a leading cause of cardiovascular mortality in this group.

There is therefore a need to provide methods to reduce the risk of development of gestational diabetes and impaired glucose tolerance in pregnant women

SUMMARY OF THE INVENTION

The inventors have conducted a study investigating the effect of a daily oral supplement containing probiotic bacteria on plasma glucose concentration and insulin sensitivity during and after pregnancy in conjunction or not with dietary counselling. They have further investigated the efficacy of specific probiotic bacterial strains and combinations of strains. During these studies, it was surprisingly found that plasma glucose concentrations were lower and insulin sensitivity was improved in the probiotic supplemented group, particularly during the third trimester of pregnancy. It was further found that post partum body composition of the probiotic supplemented group differed from that of the other groups in that body fat as evidenced by skin fold thickness and waist circumference was lower in the probiotic supplemented group.

Accordingly, in a first aspect the present invention provides the use of probiotic bacteria in the manufacture of a composition for administration to a woman in at least the third trimester of pregnancy for prevention of gestational diabetes.

In a second aspect, the present invention provides the use of probiotic bacteria in the manufacture of a composition for administration to a woman in at least the third trimester of pregnancy for normalising plasma glucose concentration.

In a third aspect, the present invention provides the use of probiotic bacteria in the manufacture of a composition for administration to a woman in at least the third trimester of pregnancy for improving insulin sensitivity.

In a fourth aspect, the present invention provides the use of probiotic bacteria in the manufacture of a composition for administration to a woman in at least the third trimester of pregnancy and for at least three months after delivery for reducing the risk of development of metabolic syndrome.

The invention extends to a method of preventing gestational diabetes by providing to a woman in at least the third trimester of pregnancy in need thereof a composition containing a therapeutic amount of probiotic bacteria.

The invention further extends to a method of reducing plasma glucose concentration and/or improving insulin sensitivity in a woman in at least the third trimester of pregnancy in need thereof by providing to the pregnant woman a composition containing a therapeutic amount of probiotic bacteria.

The invention also extends to a method for reducing the risk of development of metabolic syndrome comprising administering to a woman in at least the third trimester of pregnancy in need thereof a composition containing a therapeutic amount of probiotic bacteria and continuing administration of such probiotic bacteria for at least three months after delivery.

After delivery, the composition may be administered to the infant via the breast feeding mother or the probiotic bacteria may be administered directly to the infant either in a specific formulation or in a nutritional composition such as an infant formula.

Without wishing to be bound by theory, the inventors believe that the profound impact of the gut microbiota on the physiology, immunology and metabolism of the host has only recently begun to unravel. Probiotic bacteria can process dietary polysaccharides, indigestible by human enzymes, adding both to the pool of intraluminal absorbable glucose and to locally effective short chain fatty acids which are capable of interacting between the bacteria and the host. The presence of probiotic bacteria in the gut microbiota enhances glucose absorption as has been demonstrated by conventionalizing gnotobiotic mice leading to a fast development of microvilli as well as enhanced glucose storage in adipose tissue by suppressing the Fiaf (fasting induced adipocyte factor) gene transcription leading to enhanced lipoprotein lipase activity. Thus, germ free mice are substantially leaner than conventionally raised mice even with higher energy consumption. It is reasonable to believe that improved glucose scavenging and increased storage in adipose tissue was essential during periods of food deprivation, such as were frequently endured by our ancestors. However, in the current state of nutritional abundance at least in the developed world, the indigenous bacteria can, indeed, turn into additive cause of obesity, suggesting an attractive mode for intervention by modification of microbiota and thus glucose metabolism by probiotics.

Western societies have been faced with a substantial increase in the burden of cardiovascular diseases. Metabolic syndrome which may be defined as a combination of obesity, high waist circumference, altered glucose metabolism and insulin resistance and abnormal blood lipid levels often precedes the development of cardiovascular disease.

Further, as maternal glycaemia is also associated with macrosomia and a risk of impaired glucose tolerance in the infant which may develop even when maternal glucose tolerance is within normal reference ranges, i.e. not classified as gestational diabetes mellitus, this treatment may also have beneficial effects for the infant.

BRIEF DESCRIPTION OF THE DRAWING

FIG. 1 shows the evolution of the plasma glucose concentrations of the three study groups with time from the first trimester of pregnancy to the end of the follow up at 12 months post partum.

DETAILED DESCRIPTION OF THE INVENTION

In this specification, the following terms have the following meanings:—

"infant" means a child under the age of 12 months.

"probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

All references to percentages are percentages by weight unless otherwise stated.

The probiotic bacteria are administered to the pregnant woman during at least the third trimester of pregnancy. Preferably, however, they are administered also during the second trimester and even more preferably for the full duration of the pregnancy.

Administration of the probiotic may continue after delivery for the first four to six months of the life of the infant. After delivery, administration may be either via the breast feeding mother or directly to the infant.

The probiotic bacteria may be any lactic acid bacteria or Bifidobacteria with established probiotic characteristics having particular regard to adhesion and competitive exclusion properties. Suitable probiotic lactic acid bacteria include *Lactobacillus rhamnosus* ATCC 53103 obtainable inter alia from Valio Oy of Finland under the trade mark LGG and *Lactobacillus rhamnosus* CGMCC 1.3724. Suitable probiotic Bifidobacteria strains include *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V and the strain of *Bifidobacterium breve* sold by Institut Rosell (Lallemand) under the trade mark R0070.

CNCM I-3446 was deposited according to the Treaty of Budapest with the Pasteur Institute (28 rue du Doctor Roux, F-75024 Paris cedex 15) on Jun. 7, 2005.

Preferably, a mixture of probiotic lactic acid bacteria and Bifidobacteria is used. A particularly preferred mixture is equal quantities of *Lactobacillus rhamnosus* CGMCC 1.3724 and *Bifidobacterium lactis* CNCM I-3446.

A suitable daily dose of the probiotic bacteria is from 10e5 to 10e12 colony forming units (cfu), more preferably from 10e7 to 10e11 cfu.

The probiotic bacteria may be administered to both the pregnant woman before birth and to the mother after birth as a supplement in the form of tablets, capsules, pastilles, chewing gum or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

Alternatively, the probiotic bacteria may be administered to pregnant women in the form of a therapeutic nutritional composition. The composition may be a nutritionally complete formula.

A nutritionally complete formula for administration to pregnant women according to the invention may comprise a source of protein. Any suitable dietary protein may be used for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The composition may also contain a source of carbohydrates and a source of fat.

If the formula includes a fat source in addition to the DHA, the fat source preferably provides 5% to 40% of the energy of the formula; for example 20% to 30% of the energy. A suitable fat profile may be obtained using a blend of canola oil, corn oil and high-oleic acid sunflower oil.

A source of carbohydrate may be added to the formula. It preferably provides 40% to 80% of the energy of the formula. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of galacto-oligosaccharides with short chain fructo-oligosaccharides. Preferably, if fibre is present, the fibre content is between 2 and 40 g/l of the formula as consumed, more preferably between 4 and 10 g/l.

The formula may also contain minerals and micronutrients such as trace elements and vitamins in accordance with the recommendations of Government bodies such as the USRDA. For example, the formula may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 μg Vitamin D, 3 to 10 IU Vitamin E.

One or more food grade emulsifiers may be incorporated into the formula if desired; for example diacetyl tartaric acid esters of mono- and di-glycerides, lecithin and mono- and di-glycerides. Similarly suitable salts and stabilisers may be included.

The formula is preferably enterally administrable; for example in the form of a powder for re-constitution with milk or water.

The probiotic bacteria may be conveniently administered to infants in an infant formula. An infant formula for use according to the present invention may contain a protein source in an amount of not more than 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

The infant formula may contain a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as fibres, lactoferrin, nucleotides, nucleosides, and the like.

Both the infant formula and the nutritional formula described above may be prepared in any suitable manner. For example, they may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

The selected probiotic bacteria may be cultured according to any suitable method and prepared for addition to the nutritional or infant formula by freeze-drying or spray-drying for example. Alternatively, bacterial preparations can be bought from specialist suppliers such as Christian Hansen and Valio already prepared in a suitable form for addition to food products such as nutritional and infant formulas. The probiotic bacteria may be added to the formula in an amount between 10e3 and 10e12 cfu/g powder, more preferably between 10e7 and 10e12 cfu/g powder.

The invention will now be further illustrated by reference to the following examples:—

EXAMPLE 1

An example of a shelf stable nutritional supplement to be used according to the present invention is as follows:—

|  | Per 100 kcal | Per 100 g ready to drink | Per serving (190 ml) |
| --- | --- | --- | --- |
| Energy (kcal) | 100 | 65 | 130 |
| Fat (g) | 0.92 | 0.60 | 1.20 |
| Protein (g) | 3.54 | 2.30 | 4.60 |
| Carbohydrate (g) | 19.4 | 12.60 | 25.2 |
| Dietary fibre (g) | 3.62 | 2.35 | 4.70 |

-continued

|  | Per 100 kcal | Per 100 g ready to drink | Per serving (190 ml) |
|---|---|---|---|
| Minerals |  |  |  |
| Sodium (mg) | 51 | 33 | 66 |
| Potassium (mg) | 238 | 155 | 310 |
| Chloride (mg) | 123 | 80 | 160 |
| Calcium (mg) | 308 | 200 | 400 |
| Phosphorus (mg) | 162 | 105 | 210 |
| Magnesium (mg) | 58.0 | 38 | 76 |
| Selenium (µg) | 7.7 | 5.0 | 10.0 |
| Vitamins |  |  |  |
| Beta carotene (µg) | 1600 | 1050 | 2100 |
| Vitamin D (µg) | 3.8 | 2.50 | 5.0 |
| Vitamin E (IU) | 4.6 | 3.0 | 6.0 |
| Vitamin C (mg) | 38 | 25 | 50 |
| Vitamin B1 (mg) | 1.2 | 0.75 | 1.5 |
| Vitamin B2 (mg) | 1.3 | 0.85 | 1.7 |
| Niacin (mg) | 12 | 8 | 16 |
| Vitamin B6 (mg) | 1.1 | 0.7 | 1.4 |
| Folic acid (µg) | 310 | 200 | 400 |
| Vitamin B12 (µg) | 1.2 | 0.75 | 1.5 |
| Biotin (µg) | 54 | 35 | 70 |
| Trace Elements |  |  |  |
| Iron (mg) | 12 | 7.5 | 15 |
| Iodine (µg) | 150 | 100 | 200 |
| Copper (mg) | 0.20 | 0.13 | 0.26 |
| Zinc (mg) | 3.8 | 2.5 | 5.0 |
| Probiotic bacteria |  |  |  |
| L. rhamnosus ATCC 53103 |  |  | 10e10 |
| B-lactis Bb12 |  |  | 10e10 |

EXAMPLE 2

This example compares the effect on plasma glucose concentration and insulin sensitivity of administering probiotic bacteria to pregnant women with the effect of administration of a placebo to a comparable group of pregnant women.

256 pregnant women were recruited to participate in a randomized, prospective combined dietary counselling and probiotics intervention study (NCT00167700, http://www.clinicaltrials.gov). Subjects were recruited during the first trimester of pregnancy at their first visit to maternal welfare clinics in the city of Turku and neighbouring areas in South-West Finland. Subjects included had no metabolic diseases. Written informed consents were obtained from the women and the study protocol was approved by the Ethics Committee of the Hospital District of South-West Finland.

Study Design and Conduct

Study visits took place at each trimester of pregnancy, and at 1, 6, and 12 months postpartum. At baseline, subjects were randomly assigned to three study groups, two with 85 members and one with 86 members. Group 1 (n=85) received probiotic capsules with dietary counselling (diet/probiotics), Group 2 (n=86) received a placebo with dietary counselling (diet/placebo) and Group 3 (n=86) received a placebo with no dietary counselling (control/placebo).

Randomization to receive probiotics (*Lactobacillus rhamnosus* GG, ATCC 53103, Valio Ltd., Helsinki, Finland and *Bifidobacterium lactis* Bb12, Chr. Hansen, Hoersholm, Denmark, 10e10 cfu/day each) or placebo (anhydrous microcrystalline cellulose and dextrose, Chr. Hansen, Hoersholm, Denmark) in the dietary counselling groups took place in a double-blind manner while the control group received the placebo in single-blind manner. Administration of the probiotics started at the first study visit and lasted until the end of exclusive breastfeeding.

The activity of the probiotics was confirmed by regular analysis of microbial content and the compliance in the consumption of the capsules was assessed by interviews. Compliance in consumption of study capsules was assessed by interview. Altogether 97.8% reported having consumed the capsules daily. On initiation of capsule consumption 6.3% of the women reported gut-associated symptoms including flatulence, loose stools or constipation, but also more regular bowel function was related to capsule consumption in all three groups alike. Thereafter the prevalence of reported symptoms was reduced to 1.3% and 0.4% at subsequent study visits.

Dietary counselling for Groups 1 and 2 was given by a dietician at each study visit with the intention of modifying dietary intake to conform with that currently recommended, particular attention being paid to the quality of dietary fat. Achievement of the recommended diet was supported by providing participants with readily available food products with suitable fat composition (e.g. rapeseed oil-based spreads and salad dressings) to be consumed at home. The dietary intake was assessed at each trimester using 3-day food diaries. Energy and nutrient intakes were calculated with a Micro-Nutrica® computerized program (version 2.5, Research Centre of the Social Insurance Institution, Turku, Finland).

At baseline, background information concerning education and parity was collected by interviews. Weights and heights were measured, pre-pregnancy weight self-reported and used to calculate pre-pregnancy body mass index (BMI) as weight (kg) divided by the square of height (m). Total gestational weight gain was calculated by subtracting self reported pre-pregnancy weight from the weight recorded at prenatal visit or at hospital within one week before delivery. Information regarding infants' birth weights and heights and the course of pregnancy were obtained from hospital records. In the morning of each visit, 10 hour overnight fasting blood samples were drawn from an antecubital vein.

Biceps skin fold thickness was measured at the first visit and at the 1, 6 and 12 months post partum visits and waist circumference was measured at the 6 and 12 months post partum visits.

Analytical Methods

Plasma glucose concentration was measured with an enzymatic method utilising hexokinase by Modular P800 automatic analyser (Roche Diagnostics GmbH, Mannhein, Germany). Blood glycated haemoglobin A1C was measured with ion-exchange high-performance liquid chromatography (HPLC) by Bio-Rad Variant™ II Haemoglobin A1C Program (Bio-Rad Laboratories, Marnes-1a-Coquette, France). Serum insulin concentration was measured with an immuno-electrochemiluminometric assay (ECLIA) by Modular E 170 automatic analyser (Roche Diagnostics GmbH). To evaluate insulin sensitivity, quantitative insulin sensitivity check index (QUICKI) was calculated as described by Katz et al 14. Homeostasis model assessment (HOMA) was calculated using a formula by Matthews et al 15. Glucose challenge screening tests were performed at well-women clinics according to standard procedures for women fulfilling criteria for at risk pregnancies (pre-pregnancy BMI over 25, age over 40 yrs, gestational diabetes mellitus during previous pregnancy, previous delivery of child who weighed more than 4500 g, detection of glucose in urine or suspect of macrosomic foetus in present pregnancy) at 28 to 30 weeks of gestation.

Plasma glucose concentrations above 4.8 mmol/l during pregnancy and 5.6 mmol/l in non-pregnant state, a percentage of glycated haemoglobin versus total haemoglobin above 6.5% and serum insulin concentration above 26 mU/1 are considered heightened (Turku University Central Laboratories). Improved insulin sensitivity was evaluated by higher QUICKI and lower HOMA values. Results of the glucose challenge tests were considered pathological if heightened fasting glucose value (>4.8 mmol/l) was combined with at least one abnormal postprandial measurement (postprandial blood glucose >10.0 mmol/l at one hour or >8.7 mmol/l at two hours).

Statistical Analyses

The primary outcome measure was maternal glucose metabolism, characterized by plasma glucose concentration, blood glycated haemoglobin A1C, serum insulin and HOMA and QUICKI indices. The measurements were performed at the first trimester (baseline) and third trimester of pregnancy, and at 1, 6 and 12 months postpartum. Missing values (at most one during pregnancy and one during the postpartum period) were computed using the group mean or geometric mean, as linear extrapolation or interpolation methods were not appropriate due to the substantial inherent non-linear within-subject fluctuation. Comparison of glucose metabolism at the third trimester of pregnancy or at 12 months postpartum between the three study groups was made by analysis of covariance (ANCOVA) and the postpartum period (1, 6 and 12 mo) was analyzed using ANCOVA for repeated measurements. In both analyses the baseline was included as a continuous covariate. Serum insulin and HOMA were skewed to the right and were logarithmically transformed before analysis. The results are given as baseline-adjusted means or geometric means with 95% confidence intervals (CI). Paired group comparisons were performed Bonferroni-adjusted. Proportions of subjects with elevated glucose concentrations (≥4.8 mmol/l during pregnancy, ≥5.6 mmol/l postpartum) were compared between study groups using the Chi-square test. Results of group comparisons are given as odds ratios (OR) with 95% CI.

In addition, dietary energy-yielding nutrients assessed from food diaries were analysed to explain changes in glucose metabolism. The study groups were compared at the third trimester, during the postpartum period and at 12 months postpartum using the same methods as described for the primary outcome.

The baseline variables were analyzed using Chi-square test, ANOVA, Kruskal-Wallis test (5' Apgar) or ANCOVA for repeated measurements (weight and BMI).

Data were randomized and analyzed with SPSS (version 14.0; SPSS Inc, Chicago, Ill., USA) by a statistician (TP) independent of clinical evaluations.

Results

81% of the recruited women (208/256) were followed up until 12 months postpartum. The reasons for discontinuing were descriptive of a normal population of pregnant women. Of the 208 women completing the follow-up, 23 were pregnant again by the end of the follow up. At each time point of evaluation, to complete the longitudinal analytical series for biochemical variables 3 to 7 values were estimated resulting in a final number of 66 subjects in Group 1, 70 in Group 2 and 65 in group 3.

The participating women were Caucasian, the majority had received higher education (79% in Group 1, 69% in Group 2 and 79% in Group 3) and were expecting their first child (65% in Group 1, 51% in Group 2 and 57% in Group 3). The infants were delivered at term and their mean heights and weights were within population reference ranges. According to the mean body mass indices (BMI) prior to pregnancy, the women were of normal weight. There was no distinction between the groups in terms of pregnancy weight gain, baseline adjusted weights during pregnancy or postpartum BMI. The mean duration of exclusive breast-feeding and thus the duration of probiotics/placebo intervention did not differ amongst the study groups.

The characteristics of the women and their infants are shown in Table 1 below:—

TABLE 1

Characteristics of the women and their infants[1].

| Women | Control/placebo (n = 85) | Diet/placebo (n = 86) | Diet/probiotics (n = 85) | P value[2] |
|---|---|---|---|---|
| Age (yrs) | 30.2 (5.0) | 30.1 (5.2) | 29.7 (4.1) | 0.813 |
| Weight (kg) | | | | |
| 1$^{st}$ trimester of pregnancy (baseline) | 68.9 (11.8) | 71.0 (13.1) | 64.9 (9.7) | 0.003 |
| 3$^{rd}$ trimester | 78.4 (12.2) | 79.5 (11.0) | 74.8 (10.1) | 0.790 |
| gain over pregnancy | 14.8 (5.1) | 14.8 (5.1) | 15.0 (4.3) | 0.946 |
| BMI (kg/m$^2$) | | | | |
| prior pregnancy | 23.7 (3.5) | 24.3 (4.4) | 22.9 (3.2) | 0.037 |
| 1$^{st}$ trimester of pregnancy (baseline) | 24.7 (3.6) | 25.4 (4.7) | 23.7 (3.2) | 0.017 |
| postpartum[3] | 25.7 (3.6) | 25.9 (4.2) | 24.6 (3.1) | |
| | 25.2 (3.9) | 25.6 (5.0) | 23.8 (3.4) | |
| 1 mo | 24.8 (3.9) | 25.1 (5.3) | 23.4 (3.3) | 0.975[4] |
| 6 mo | 3.4 (1.6) | 3.6 (1.9) | 3.3 (1.8) | 0.587 |
| 12 mo | 8.3 (4.5) | 9.1 (5.8) | 7.6 (4.3) | 0.287 |
| Duration (mo) of exclusive breast-feeding | | | | |
| total breast-feeding | | | | |
| Infants[5] | 40.1 (1.3) | 39.9 (1.8) | 39.9 (1.3) | 0.672 |
| Birth at weeks of gestation | 3600 (515) | 3602 (439) | 3489 (431) | 0.209 |
| Birth weight (g) | 51 (2) | 51 (2) | 51 (2) | 0.197 |

TABLE 1-continued

Characteristics of the women and their infants[1].

| Women | Control/placebo (n = 85) | Diet/placebo (n = 86) | Diet/probiotics (n = 85) | P value[2] |
|---|---|---|---|---|
| Birth height (cm) | 35.1 (1.4) | 35.1 (1.3) | 34.8 (1.3) | 0.257 |
| Head circumference (cm) | 9 (4-10) | 9 (3-10) | 9 (6-10) | 0.280[6] |
| Apgar at 5 min | | | | |

[1]Results are given as mean (SD) or median (range).
[2]ANOVA or ANCOVA, where baseline was included as a covariate when appropriate (weight and BMI).
[3]pregnant mothers were excluded from analysis.
[4]ANOVA for repeated measurements (1, 6 and 12 mo).
[5]n = 76-78 in control/placebo, n = 76-79 in diet/placebo and n = 75-81 in diet/probiotics.
[6]Kruskal-Wallis test.

Impact of Intervention on Glucose Metabolism

In all study groups the plasma glucose concentrations decreased from the first trimester to the third trimester and increased during the 12 month postpartum period (FIG. 1). The difference between the study groups was significant during pregnancy, when the baseline-adjusted means were 4.56, 4.60 and 4.45 mmol/l in Group 3, Group 2 and Group 1, respectively (p=0.025), almost significant at 12 months after delivery (adjusted mean values 5.06, 5.22 and 4.93 mmol/l; p=0.060) and significant over postpartum period up to 12 months after delivery (adjusted means 5.02, 5.01 and 4.87 mmol/l; p=0.025). Group 1 was distinguishable from Group 2 at the third trimester of pregnancy (p=0.026), at 12 months postpartum (p=0.054) and over the entire postpartum period (p=0.066), and further from Group 3 over the postpartum period (p=0.048).

Although mean plasma glucose concentrations were within normal reference ranges in all study groups, the risk of elevated glucose concentration was reduced in Group 1 throughout the study period (FIG. 1, insert). During the third trimester, the intervention of Group 1 had the capacity to reduce the risk of high plasma glucose concentrations (>4.8 mmol/l) (OR 0.31, 95% CI 0.12 to 0.78; p=0.013) compared with Group 3. However, the intervention of Group 2 did not have this capacity compared with Group 3 (OR 1.26, 95% CI 0.59 to 2.69; p=0.553). Albeit not statistically significant, the risk of high plasma glucose concentrations (>5.6 mmol/l) persisted less in Group 1 over the post partum period (OR=0.46, 95% CI 0.14 to 1.50; p=0.197), but not in Group 2 (OR 1.55, 95% CI 0.61 to 3.95; p=0.360) compared to Group 3.

45% of the subjects underwent a glucose challenge test during pregnancy. Although the prevalence of pathological test results was lowest in Group 1 (37% of subjects) compared to Group 2 (58%) and Group 3 (57%), the relative risk was not significantly lowered.

Glycated haemoglobin A1C remained within normal ranges throughout the study in all but one subject participating in the Group 2 at 12 months postpartum. Whilst mean glycated haemoglobin A1C were comparable amongst the study groups at the third trimester of pregnancy and 12 months postpartum, there was a tendency for lowered glycated haemoglobin A1C in Group 1 compared to Group 2 over the postpartum period (Table 2).

Impact of Intervention on Maternal Body Composition Post Partum

As noted above, there were no differences in weight gain between the groups during pregnancy. However, post partum body composition as evidenced by biceps skin fold thickness which is a measure of body fat differed between the groups as shown in Table 2 below with the lowest values being recorded for Group 1, the difference being statistically significant (p=0.03) when the measurements taken at the first visit are taken as covariant.

TABLE 2

| Biceps skin fold thickness (cm) | 1 month | 6 months | 12 months |
|---|---|---|---|
| Group 1 | 0.83 (0.33) | 0.89 (0.44) | 0.81 (0.4) |
| Group 2 | 0.97 (0.52) | 1.05 (0.6) | 0.89 (0.5) |
| Group 3 | 1.03 (0.54) | 1.13 (0.62) | 1.08 (0.65) |

Standard deviation in parentheses

Further, waist circumference which is another measure of body fat as well as being one the factors implicated in metabolic syndrome was also lower for Group 1, the difference between the groups being statistically significant over time (p=0.005). the measurements are shown in Table 3 below.

TABLE 3

| Waist circumference (cm) | 6 months | 12 months |
|---|---|---|
| Group 1 | 76.31 (7.90) | 74.90 (6.85) |
| Group 2 | 81.28 (10.89) | 80.08 (11.23) |
| Group 3 | 80.54 (9.17) | 78.75 (10.15) |

Standard deviation in parentheses

Impact of Intervention on Serum Insulin and Insulin Sensitivity Indices

Insulin concentration as well as insulin resistance evaluated by HOMA index increased and insulin sensitivity evaluated by QUICKI index reduced towards the third trimester of pregnancy in all groups. Comparably, after delivery insulin concentration and HOMA index were reduced and QUICKI index increased. Mean serum insulin concentrations, insulin resistance and insulin sensitivity were found to differ amongst the groups, throughout the study period (Table 3). This difference, at the third trimester of pregnancy and over the postpartum period, was explained by the serum insulin lowering effect of the Group 1 intervention, which was especially pronounced when compared to Group 3 at combined postpartum visits. HOMA index was lowest and QUICKI index highest, suggesting an improved insulin sensitivity in Group 1. The intervention of Group 1 proved especially beneficial compared with Group 2 during the third trimester of pregnancy and with Group 3 over the postpartum period.

This study provides the first evidence of an active dialogue between the host and the gut microbiota in glucose metabolism; combined dietary counselling and probiotic intervention may moderate plasma glucose concentration and afford glycemic control in healthy young females. Although previous studies have shown evidence of improved glucose metabolism during pregnancy by dietary means, particularly in those women with diagnosis of gestational diabetes, this study is the first to show long-term benefits on glucose and insulin metabolism of probiotics combined with dietary counselling. Probiotics appeared to bring about a more profound glucose lowering effect than dietary counselling alone suggesting that probiotics may be of particular importance.

Starting from the same study described above, the serum of the respective infants from the mothers of control group, group 1 and group 2 and has been analyzed for concentrations of "Split 32-33 Proinsulin". The measurement was performed according to a standard method described in particular in The Lancet 2003; vol. 361:1089-97 (published on Mar. 29, 2003). Samples were taken when the infants were 6 months old, blood samples were withdrawn by venepuncture before noon, serum was immediately separated and stored initially at −20° C. and then at −80° C. until analysis for 32-33 split proinsulin by time-resolved fluorometric assay (The Lancet 2003). Split 32-33 proinsulin is a partly processed from of proinsulin, higher concentration of which indicate greater insulin resistance. Greater insulin resistance is itself associated with the three well-known risk factors for metabolic disorders (obesity, diabetes, hypertension). The results are shown in table 4. The prevalence of high split 32-33 proinsulin in group 2 (intervention-placebo) is 46% of that of the controls. In group 1 (intervention-probiotic group) the prevalence of high split 32-33 proinsulin is 37% of that seen in controls.

The results indicate that the dietary intervention with probiotics is associated with a lower prevalence of high split 32-33 proinsulin in the infants. As such it is believed that the intervention can be beneficial to the infants and may reduce the risk of metabolic syndrome like overweight, diabetes and hypertension later in life.

TABLE 4

High proinsulin (>85% percentile in proinsulin or in 32-33 split proinsulin) in study groups.
Non-adjusted and adjusted[1] group comparison using logistic regression analysis.

|  | Non-adjusted | | | Adjusted[1] | | |
| --- | --- | --- | --- | --- | --- | --- |
|  | OR | 95% CI | p | OR | 95% CI | p |
| Study group |  |  | 0.066 |  |  | 0.053 |
| Group 1 | 0.46 | 0.19 to 1.10 | 0.079 | 0.43 | 0.17 to 1.12 | 0.085 |
| Group 2 | 0.37 | 0.15 to 0.94 | 0.037 | 0.30 | 0.11 to 0.86 | 0.026 |
| Dur. of breastfeeding (≥6 mo) |  |  |  | 0.22 | 0.09 to 0.50 | <0.001 |

TABLE 4-continued

High proinsulin (>85% percentile in proinsulin or in 32-33 split proinsulin) in study groups.
Non-adjusted and adjusted[1] group comparison using logistic regression analysis.

|  | Non-adjusted | | | Adjusted[1] | | |
| --- | --- | --- | --- | --- | --- | --- |
|  | OR | 95% CI | p | OR | 95% CI | p |
| Mothers glucose > median |  |  |  | 2.13 | 0.89 to 5.12 | 0.091 |

[1]The following variables were given to the stepwise logistic regression model: mothers glucose at 6 mo, diabetes during pregnancy, maternal smoking prior pregnancy and duration of breast-feeding 6 mo. Control group is the reference group.

The invention claimed is:

1. A method for reducing the risk of developing gestational diabetes comprising administering to a woman in at least the third trimester of pregnancy in need thereof, a therapeutically-effective amount of a composition comprising probiotic bacteria *Lactobacillus rhamnosus* ATCC 53103 and *Bifidobacterium lactis* CNCM I-3446.

2. The method of claim 1, wherein administration of the composition continues after delivery.

3. The method of claim 1, wherein the probiotic bacteria is administered in a daily dose of between $10^5$ to $10^{12}$ colony forming units.

4. The method of claim 1, wherein the probiotic bacteria is administered to the woman for the second and third trimesters of pregnancy.

5. The method of claim 1, wherein the probiotic bacteria is administered for the full duration of the pregnancy.

6. The method of claim 1, wherein the probiotic bacteria is administered in a daily dose of between $10^7$ to $10^{11}$ colony foaming units.

7. The method of claim 1, wherein the composition further comprises a fat source that provides 20% to 30% of the total energy of the composition, a carbohydrate source that provides 40% to 80% of the total energy of the composition, and a protein source.

8. The method of claim 1, wherein the woman to whom the composition is administered has a characteristic indicating increased risk of gestational diabetes, the characteristic selected from the group consisting of a pre-pregnancy body mass index over 25, an age over 40 years, gestational diabetes mellitus during a previous pregnancy, a previous delivery of a child who weighed more than 4500 g, detection of glucose in urine, suspect of macrosomic fetus in present pregnancy, and combinations thereof.

* * * * *